United States Patent [19]

Adembri et al.

[11] 3,944,563
[45] Mar. 16, 1976

[54] 1-AMINO-PYRAZOLIC DERIVATIVES

[75] Inventors: Giorgio Adembri; Piero Tedeschi; Fabio Ponticelli; Maresco Marini, all of Florence, Italy

[73] Assignee: Etablissements Nativelle, S.A., Paris, France

[22] Filed: Mar. 7, 1975

[21] Appl. No.: 556,522

Related U.S. Application Data

[62] Division of Ser. No. 323,605, Jan. 15, 1973, Pat. No. 3,887,578.

[30] Foreign Application Priority Data

Jan. 14, 1972 United Kingdom............... 01864/72

[52] U.S. Cl................................. 260/310 R; 424/273
[51] Int. Cl.²............... C07D 231/46; A61K 31/415
[58] Field of Search..................... 260/310 A, 310 R

[56] References Cited
UNITED STATES PATENTS

| | | | |
|---|---|---|---|
| 3,207,763 | 9/1965 | Harder et al..................... | 260/310 R |
| 3,694,456 | 9/1972 | Noguchi et al.................. | 260/310 R |

OTHER PUBLICATIONS
Bull. Soc. Chim. [4]; No. 1, p. 234, (1907).

*Primary Examiner*—Donald B. Moyer
*Attorney, Agent, or Firm*—Sughrue, Rothwell, Mion & Zinn

[57] ABSTRACT

1-amino-5-alkoxy-pyrazole compounds of the formula:

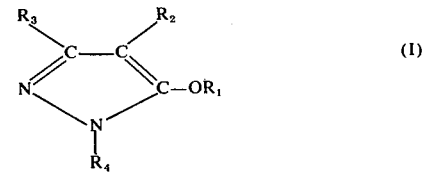

wherein $R_1$ represents a lower alkyl group having 1 to 4 carbon atoms, $R_2$ and $R_3$, which may be identical or different, represent a hydrogen atom, a lower alkyl group, a phenyl group, a phenyl group substituted by one or more groups selected from lower alkyl, halogen, nitro and lower alkoxy; $R_4$ represents an amino group, a mono-lower alkyl amino group or a di-lower alkyl amino group; as well as their salts with a mineral or organic acid.

A method for the preparation thereof, consisting essentially in internally transforming, in the presence of hydrazine, a 5-hydrazino-isoxazole (or 5-halogenoisoxazole) derivative and alkylating the 5-hydroxy-derivative obtained with a suitable diazoalkane.

3 Claims, No Drawings

1-AMINO-PYRAZOLIC DERIVATIVES

This application is a division of applicants' copending application Ser. No. 323 605 filed Jan. 15, 1973 now U.S. Pat. No. 3,887,578.

The present invention relates to new and useful 1-amino-5-alkoxy-pyrazole compounds corresponding to the general formula (I):

1-amino-5-alkoxy-pyrazole compounds of the formula:

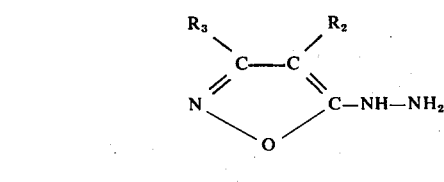

(I)

wherein $R_1$ represents a lower alkyl group having 1 to 4 carbon atoms, $R_2$ and $R_3$, which may be identical or different, represent a hydrogen atom, a lower alkyl group, a phenyl group, a phenyl group substituted by one or more groups selected from lower alkyl, halogen, nitro and lower alkoxy; $R_4$ represents an amino group, a mono-lower alkyl amino group or a di-lower alkyl amino group; as well as their salts with a mineral or organic acid.

The terms "lower alkyl" and "lower alkoxy" designate an alkyl or alkoxy group having 1 to 4 carbon atoms.

The invention also relates to a method for the preparation of compounds of the general formula (I) which comprises internally transforming, in the presence of hydrazine a derivative of 5-hydrazino-isoxazole of formula (II):

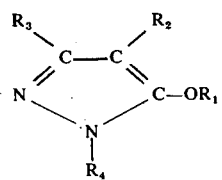

(II)

where $R_2$ and $R_3$ retain the above definition, which may be prepared in situ from a 5-halogeno-isoxazole treated with hydrazine, according to the process described in the copending application Ser. No. 323,605 filed Jan. 15, 1973. The 5-hydroxy derivatives isolated from the products thus obtained are then alkylated with a suitable alkylation agent, such as diazomethane in order to produce the 1-amino-5-alkoxy-pyrazole compounds of formula (I)

The invention also relates to a method for preparing salts of compounds of general formula (I). This method consists in causing the corresponding mineral or organic acids to act on these compounds.

The new 1-amino-5-alkoxy-pyrazole compounds of general formula (I) and their pharmaceutically acceptable organic or mineral acid salts according to the present invention have an anti-depressive, analgesic, anti-histaminic and spasmolytic effect.

The compounds according to the general formula (I) where $R_4$ represents $NH_2$ may be prepared by the following method:

A 5-hydroxy derivatives is first prepared from a suitable derivative of 5-hydrazino-isoxazole by internal transposition in the presence of hydrazine, according to the following scheme:

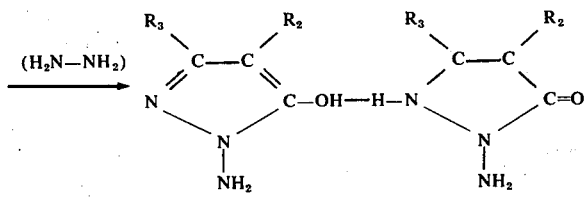

5-hydrazino-isoxazole may be prepared in situ by causing a 5-halogeno-isoxazole to react with anhydrous hydrazine.

The reaction is advantageously effected by dissolving 1 mole of 5-hydrazino-isoxazole in a large quantity, preferably 20–30 moles, of anhydrous hydrazine and by heating the solution for 2 to 2,5 hours at 90° – 100°C.

The 5-hydroxy derivatives isolated from the products of the internal transposition hereabove described are alkylated by a suitable diazoalkane. Alkylation is preferably obtained by dissolving 1 mole of 1-amino-5-hydroxy-pyrazole in a very small amount of methanol and adding an excess amount, preferably 2 to 2,5 moles, of diazoalkane in an ether solution.

The compounds according to the general formula (I) in which $R_1$ is an alkyl group and $R_4$ an amino group disubstituted by two identical or different alkyl groups, are prepared by alkylation of the compounds obtained as hereabove described by a suitable alkyl halide or dialkyl sulfate. The proportion of 1-amino-5-alkoxy-pyrazole to alkylation agent varies according to whether it is desired to produce di-alkylation of the nitrogen of the amino group bonded to the pyrazolic ring in position 1. If it is wished to obtain different alkyl groups as substituents on the nitrogen of the amino group, two different monoalkylations must be effected with different alkyl halides or sulfates.

Alkylation by alkyl halides is preferably effected by treating 1-amino-5-alkoxy-pyrazole in an alcoholic solution, with an alkyl halide in the presence of a sodium alcoholate, keeping the solution under reflux for 1 – 2 hours.

Alkylation by di-alkyl sulfates is preferably effected by treating 1-amino-5-alkoxy-pyrazole, in an alcoholic solution, with an excess amount of di-alkyl sulfate in the presence of an alkaline hydrate, under reflux, at 60° – 80°C, for 3 – 4 hours.

The following examples illustrate the invention without limiting the same:

EXAMPLE 1

1-amino-3-phenyl-4-methyl-5-methoxy-pyrazole $R_4 = NH_2; R_3 = C_6H_5; R_2 = CH_3; R_1 = CH_3$ 10 g of 3-phenyl-4-methyl-isoxazolyle-5-hydrazine are treated with 50ml anhydrous hydrazine, and the solution is heated for 3 hours. The solution is concentrated until a limited volume is obtained. It is then diluted with water and extracted with ether. The aqueous stage is treated with active carbon. It is filtered and acidified to a pH 5 – 6 with concentrated hydrochloric acid. It is allowed to stand in the refrigerator and 6 g of 1-amino-3-phenyl-4-methyl-5-hydroxy-pyrazole is obtained. This is recovered with methanol and treated with 2.5 g diazomethane in an etheralcohol solution.

After evaporation of the ethereal solution, a residue is obtained which is extracted repeatedly when heated, with ligroin. After decanting and cooling the solution, 1-amino-3-phenyl-4-methyl-5-methoxy-pyrazole is obtained. After crystallization in the ligroin and purification by sublimation in a vacuum, the product has a melting point of 92° –94°C.

| Analysis   | : | $C_{11}H_{13}N_3O$ |         |           |
|------------|---|--------------------|---------|-----------|
| Calculated | : | C 65.01 %          | H 6.45 %| N 20.67 % |
| Found      | : | C 65.28 %          | H 6.50 %| N 20.96 % |

EXAMPLE 2

By using the same method as described in example 1 the following compounds have been prepared:

1-amino-3-phenyl-5-methoxy-pyrazole obtained from the corresponding 3-phenyl-isoxazolyl-5-hydrazine. This product has a melting point of 158°–160°C.

1-amino-3 methyl-4-phenyl-5-methoxy-pyrazole obtained from the corresponding 3-methyl-4-phenyl-isoxazolyl-5-hydrazine. This product has a melting point of 93°–94°C.

PHARMACOLOGICAL STUDY

The products according to the present invention have a depressive effect on the central nervous system. This depressive effect is manifested by a sedative and myorelaxant action. These products also have analgesic, anti-histaminic and spasmolytic effects.

The study showed, for example, that the product 1-amino-3-phenyl-5-methoxy-pyrazole has a depressive action on the central nervous system, consisting in a sedative, myorelaxant and anti-convulsive effect. This product also has a marked spasmolytic effect. The study was carried out on mice, rats and dogs.

The average lethal dose ($LD_{50}$) taken orally by mice is ca. 1000 mg/kg.

PHARMACEUTICAL COMPOSITIONS

The new compounds according to the present invention may be administered in the conventional ways: orally, peritoneally, rectally, diluted in supports utilized in the pharmaceutical field, for example, in the form of gels, capsules, compressed tablets, pills, sirups, emulsions, solutions, injections and suppositories.

Lactose, amidon, polyvinylpyrrolidone, magnesium stearate, talc, microcrystalline cellulose, and/or carboxymethylcellulose, may be used as solid diluents for the preparation of the compressed tablets.

Bi-distilled water, a mixture of bi-distilled water and propyleneglycol, and propylene glycol may be used as diluents in the preparation of injectable solutions.

The following compounds are particularly suitable for use as solid diluents in the preparation of suppositories: triglycerides, saturated fatty acids, cocoa butter and polyethyleneglycol.

All formulations suitable for these administration methods, may be used. The medicament is used as an active constituent with a pharmaceutically acceptable vehicle.

The following formulation is provided by way of example as being suitable for the preparation of compressed tablets:

| 1-amino-3-phenyl-4-methyl-5-methoxy-pyrazole | 100 mg |
| Lactose | 100 mg |
| Amidon | 60 mg |
| Polyvinylpyrrolidone | 8 mg |
| Talc | 4 mg |
| Magnesium stearate | 3 mg |

The following are suitable formulations for preparing injectable solutions:

1. 1-amino-3-phenyl-4-methyl-5-methoxy-pyrazole  50 mg
   Propylene glycol  1 ml
   Bi-distilled water (sterile and apyrogenic)
   to make  2 ml
   pH of the solution 5.7
2. 1-amino-3-phenyl-4-methyl-5-methoxy-pyrazole  200 mg
   Benzyl alcohol  0.1 ml
   Peanut oil
   to make  2 ml The following may be used in the preparation of suppositories:

1-amino-3-phenyl-4-methyl-5-methoxy-pyrazole  50 mg
Triglycerides of satured fatty acids
to make  1.5 g

What is claimed is:

1. 1-amino-5 alkoxy-pyrazole compounds of the formula:

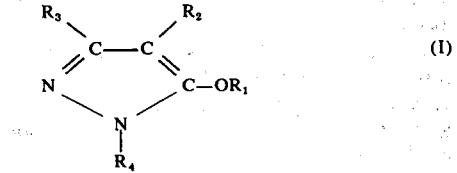

(I)

wherein $R_1$ represents a lower alkyl group having 1 to 4 carbon atoms, $R_2$ and $R_3$, which may be identical or different, represent a hydrogen atom, a lower alkyl group, a phenyl group, a phenyl group substituted by one or more groups selected from lower alkyl, halogen, nitro and lower alkoxy; $R_4$ represents an amino group, a mono-lower alkyl amino group or a di-lower alkyl amino group; as well as their pharmaceutically acceptable salts with a mineral or organic acid.

2. A compound as defined in claim 1 wherein said compound is: 1-amino-3-phenyl-5-methoxy-pyrazole.

3. A compound as defined in claim 1 wherein said compound is: 1-amino-3-phenyl-4-methyl-5-methoxy-pyrazole.

* * * * *